US 11,481,728 B2

(12) United States Patent
Lang et al.

(10) Patent No.: US 11,481,728 B2
(45) Date of Patent: Oct. 25, 2022

(54) RADIATION THERAPY KNOWLEDGE EXCHANGE

(71) Applicants: Burton Lang, Palo Alto, CA (US); Corey Zankowski, San Jose, CA (US); Ramin Baghaie, Espoo (FI)

(72) Inventors: Burton Lang, Palo Alto, CA (US); Corey Zankowski, San Jose, CA (US); Ramin Baghaie, Espoo (FI)

(73) Assignees: VARIAN MEDICAL SYSTEMS, INC., Palo Alto, CA (US); VARIAN MEDICAL SYSTEMS INTERNATIONAL AG, Cham (CH)

( * ) Notice: Subject to any disclaimer, the term of this patent is extended or adjusted under 35 U.S.C. 154(b) by 0 days.

(21) Appl. No.: 16/451,381

(22) Filed: Jun. 25, 2019

(65) Prior Publication Data
US 2019/0385260 A1 Dec. 19, 2019

Related U.S. Application Data

(63) Continuation of application No. 13/016,842, filed on Jan. 28, 2011, now Pat. No. 10,332,225.

(51) Int. Cl.
*G06Q 10/10* (2012.01)
*G16H 80/00* (2018.01)
*G16H 50/70* (2018.01)
*G16H 70/20* (2018.01)

(52) U.S. Cl.
CPC ............ *G06Q 10/10* (2013.01); *G16H 50/70* (2018.01); *G16H 70/20* (2018.01); *G16H 80/00* (2018.01)

(58) Field of Classification Search
CPC .............................. G06Q 10/10; G06Q 50/22
See application file for complete search history.

(56) References Cited

U.S. PATENT DOCUMENTS

| 7,158,692 | B2 * | 1/2007 | Chalana | ............... G16Z 99/00 |
| | | | | 382/128 |
| 7,817,836 | B2 | 10/2010 | Chao et al. | |
| 7,844,560 | B2 * | 11/2010 | Krishnan | ............... G16H 20/40 |
| | | | | 706/46 |
| 7,995,813 | B2 | 8/2011 | Foshee et al. | |

(Continued)

FOREIGN PATENT DOCUMENTS

| CN | 1393815 | 1/2003 |
| CN | 1592293 | 3/2005 |

(Continued)

*Primary Examiner* — Robert A Sorey
*Assistant Examiner* — Kristine K Rapillo (57) ABSTRACT

A method for implementing a radiation therapy knowledge exchange starts with searching a database of cases studies and selecting a case study. The selected case study is downloaded. The downloaded case study is applied to a medical case, wherein the downloaded case is applied using deformable image registration to deform reference images of the downloaded case to medical images of the medical case. After application of the downloaded case study, the medical case is uploaded to the network, wherein uploading the medical case allows at least the submitting clinician to download, review, and edit at least a portion of the medical case to create a reviewed medical case. Finally, the reviewed medical case is downloaded and applied to the medical case to create a final medical case.

18 Claims, 5 Drawing Sheets

(56) References Cited

U.S. PATENT DOCUMENTS

| | | |
|---|---|---|
| 8,199,990 B2 | 6/2012 | Foshee et al. |
| 2005/0010098 A1* | 1/2005 | Frigstad .................. A61B 6/00 600/407 |
| 2005/0041843 A1 | 2/2005 | Sawyer |
| 2007/0288264 A1* | 12/2007 | Brown .................. G16H 30/20 705/2 |
| 2008/0006282 A1 | 1/2008 | Sukovic et al. |
| 2008/0270175 A1 | 10/2008 | Rodriguez et al. |
| 2009/0080734 A1 | 3/2009 | Moriya et al. |
| 2009/0125334 A1 | 5/2009 | Krishnan et al. |
| 2009/0208076 A1 | 8/2009 | Nakajima et al. |
| 2010/0022655 A1 | 1/2010 | Byrd et al. |
| 2010/0067769 A1 | 3/2010 | Neemuchwala et al. |
| 2010/0205007 A1 | 8/2010 | Meesa et al. |
| 2010/0226550 A1 | 9/2010 | Miyasa et al. |
| 2011/0007959 A1 | 1/2011 | Schulz et al. |
| 2011/0015941 A1 | 1/2011 | Backhaus |
| 2011/0022622 A1 | 1/2011 | Boroczky et al. |
| 2011/0153547 A1 | 6/2011 | McNutt et al. |
| 2011/0188718 A1* | 8/2011 | Hill .................. G16H 30/20 382/128 |

FOREIGN PATENT DOCUMENTS

| | | |
|---|---|---|
| CN | 1742275 | 3/2006 |
| CN | 101271489 | 9/2008 |
| CN | 101820948 | 9/2010 |
| WO | 0225588 | 3/2002 |
| WO | 2008057229 | 5/2008 |
| WO | 2009055801 | 4/2009 |

* cited by examiner

RADIATION THERAPY KNOWLEDGE EXCHANGE

This application is a continuation application of Ser. No. 13/016,842, entitled "Radiation Therapy Knowledge Exchange," by Lang et al., filed Jan. 28, 2011, now U.S. Pat. No. 10,332,225, which is incorporated herein by reference in its entirety.

TECHNICAL FIELD

The present disclosure relates generally to the field of radiation therapy and more specifically a collaborative exchange of knowledge for improving best practices in radiation therapy.

BACKGROUND

Oncology and Radiotherapy technology continues to evolve, accelerating the expansion of the envelope of possible treatments and best practices associated with those possible treatments. At the same time, the complexity of clinical decisions is increasing non-linearly, resulting in a rapidly widening gap between actual practice and best practices, especially in emerging markets.

For example, when medical imaging is necessary in the course of radiation therapy, several systems may be used, such as X-ray, magnetic resonance imaging (MRI), computed tomography (CT), and others. When CT or MRI imagery, for example, is used, a series of two-dimensional images are taken from a three-dimensional volume. Here, each two-dimensional image is an image of a cross-sectional "slice" of the three-dimensional volume. The resulting collection of two-dimensional cross-sectional slices can be combined to create a three-dimensional image or reconstruction of the patient's anatomy. This resulting three-dimensional image or three-dimensional reconstruction will contain organs of interest. Those organs of interest include the organ targeted for radiation therapy, as well as other organs that may be at risk of radiation therapy exposure. The portion of the three-dimensional image or reconstruction that contains the organs of interest may be referred to as structures of interest or volumes of interest.

These one or more structures of interest may be viewed in several ways. A first and simplest way to view the structure(s) of interest would be to merely view the original CT or MRI image slices for the patient, with each slice containing a view of the structure(s) of interest. A second, and more complicated method to view the structure(s) of interest would be to combine the series of two-dimensional cross-sectional slices into a single three-dimensional representation where the structure(s) of interest may be represented as solid, opaque, or translucent, etc., objects that may then be manipulated (e.g., rotated) to allow viewing from multiple angles.

One purpose of the three-dimensional reconstruction of the structure(s) of interest containing diseased or abnormal tissues or organs is the preparation of a three-dimensional radiation therapy treatment plan. Radiation therapy treatment plans are used during medical procedures that selectively expose precise areas of the body, such as cancerous tumors, to specific doses of radiation to destroy the undesirable tissues. To develop a patient-specific radiation therapy treatment plan, information is extracted from the three-dimensional model to determine parameters such as organ shape, organ volume, tumor shape, tumor location in the organ, and the position or orientation of several other structures of interest as they relate to the affected organ and any tumor.

The two-dimensional slices may be individually viewed on a computer screen and with the use of conventional graphics programs, the contours of organs or structures of interest can be traced out by hand. Contours are connected line segments that define the outline of a structure of interest, which may be an organ, a portion of an organ, a tumor, diseased tissue, or a whole patient outline. Alternatively, these structures of interest in specific organs such as the brain or prostate, for example, may be identified with various structure-specific automatic contouring and/or automatic segmentation software programs (subdividing an image into discrete regions) that outline or fill the shape of the structure of interest on each two-dimensional slice of a set of slices.

As evolving technologies provide increasingly complicated radiation therapy treatment planning possibilities, the gap between actual clinical practice and possible best practices increases. Therefore, improved methods for realizing and communicating improved results using emerging technological innovations are required.

SUMMARY OF THE INVENTION

This present invention provides a solution to the challenges inherent in achieving radiation therapy best practices. In a method according to one embodiment, a series of steps provide a knowledge-based radiation therapy exchange. The method starts by searching a database of cases studies and selecting a selected case study. The selected case study is downloaded into a tool set. The downloaded case study is applied to a medical case in the tool set, wherein the downloaded case is applied using deformable image registration to deform reference images of the downloaded case to medical images of the medical case. After application of the downloaded case study, the medical case is uploaded to the exchange, wherein uploading the medical case allows at least a clinician who contributed the selected case study to download, review, and edit at least a portion of the medical case to create a reviewed medical case. Finally, the reviewed medical case is downloaded and applied to the medical case to create a final medical case.

BRIEF DESCRIPTION OF THE DRAWINGS

The present invention will be better understood from a reading of the following detailed description, taken in conjunction with the accompanying drawing figures in which like reference characters designate like elements and in which.

DETAILED DESCRIPTION

Reference will now be made in detail to the preferred embodiments of the present invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail so as not to unnecessarily obscure aspects of the embodiments of the present invention.

Notation And Nomenclature

Some portions of the detailed descriptions, which follow, are presented in terms of procedures, steps, logic blocks, processing, and other symbolic representations of operations on data bits within a computer memory. These descriptions and representations are the means used by those skilled in the data processing arts to most effectively convey the substance of their work to others skilled in the art. A procedure, computer executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "processing" or "accessing" or "executing" or "storing" or "rendering" or the like, refer to the action and processes of a computer system, or similar electronic computing device, that manipulates and transforms data represented as physical (electronic) quantities within the computer system's registers and memories and other computer readable media into other data similarly represented as physical quantities within the computer system memories or registers or other such information storage, transmission or display devices. When a component appears in several embodiments, the use of the same reference numeral signifies that the component is the same component as illustrated in the original embodiment.

This present invention provides a solution to the increasing challenges inherent in improving and communicating radiation therapy best practices. In particular, various embodiments of the present disclosure provide a knowledge exchange allowing clinical consumers and clinical providers to share best practices in Radiation Therapy treatment including radiation therapy prescriptions, delineation of organs, tumors and regions within medical images for treatment planning (e.g., contours and segmentation of organs of interest), radiation therapy treatment planning, and radiation therapy treatment protocols, to name a few.

By creating an open knowledge exchange, users of the knowledge exchange will be able to generate and share valuable clinical content. Further, these users of the knowledge exchange will be able to collaborate to solve their own problems and share solutions with others. Further, the knowledge exchange will help accelerate the adoption of new technological developments by enabling the rapid development of clinical case examples using the new technological developments that demonstrate not only "what" to do, but also "how" and "why."

The advancement of sophisticated electronic tools employed in the field of radiation therapy allows this exchange to be in the form of editable electronic clinical files related to each of the treatment steps. Combining these electronic clinical files together around a specific clinical case enables a new method of sharing of case specific clinical best practice. Electronic clinical case files are assigned meta-data tags that allow the case files to be searched using a search engine. Such searching will allow a particular expert case to be identified by at least one identifying characteristic, such as weight, height, sex, age, race, size of patient, diagnosis, treatment site, whether or not there is nodal involvement, any co-morbidities, side of the body, and approximate location of tumor, etc. The electronic files include clinical process descriptions, or protocols, that can be combined with outcomes information to create significantly stronger statistical links between radiation therapy protocols and resulting outcomes. In particular, a clinician wishing to download an "expert" case study with similar meta-data as their patient will receive a reference image set containing the delineation of organs, tumors and regions within images (e.g., contours and segmentation of organs of interest) for treatment planning that may be applied to their own patient as described below.

Combined with widely available collaborative networking tools, the adoption of standard interfaces allowing electronic capture and transfer of clinical knowledge, and the existing paradigm of sharing content via an electronic market, a hub may be created for the creation and dissemination of Oncology knowledge. The electronic content will represent a form of intellectual property, or copywrite, held by an authoring clinician, which can be either sold or given to others on these networks.

An exemplary embodiment of the radiation therapy knowledge exchange platform will allow an author/clinician to post case files (herein also referred to as case studies) and then host a collaborative web discussion with those who download the case files about the methodology described in the case files. Sharing and discussing the electronic information can occur in either configurable public or private networks. In other words, the posted case files may be placed into a private network that only selected other clinicians/reviewers will have access to review and comment on, or the posted case files may be placed into a public network that any clinician/reviewer that is part of the knowledge exchange has access to review and comment on.

In an exemplary embodiment, other clinicians who download the case studies may review and rate the quality of the individual case studies, creating a new type of peer review process for clinical data. A group of clinicians may choose to elect a particular clinical case for collaborative refinement and promote its status to that of an "expert case," which indicates a high-level of peer review and acknowledgement of excellence from the community.

This new method of sharing and developing new best practices will supplement and enhance the existing practice of publishing papers. The benefits include direct and more explicit transfer of clinical best practice in the form of electronic templates, a platform for significantly quicker clinician to clinician discussion around how to use these techniques, and more detailed clinical process information allowing a stronger statistical link to clinical outcomes data.

In an exemplary embodiment, the knowledge exchange will consist of a web site where participants (e.g., contributing clinicians and consumer clinicians downloading case studies) can both post and download content. Access to the web site will require user identification and signing usage agreements. The web site will include a search engine that will search the knowledge-base according to meta-data categories such as: weight, height, sex, age, race, size of patient, diagnosis, treatment site, whether or not there is nodal involvement, any co-morbidities, side of the body, and approximate location of tumor, etc. Indication of the practitioner's particular clinic tool set is necessary because different clinical tool sets have different requirements that must be distinguished. For example, a RapidArc® plan assumes you have the RapidArc tools to execute it.

Knowledge Organization

The electronic clinical content will be organized around individual clinical case studies and provide an important reference and starting point for the specific patient case across the clinical process. In addition to providing contour information, the electronic content of the case study will include one or more examples of treatment plans for the same case, with the relevant care path and prescription. In one embodiment, a clinic tool set will be able to import and export to other clinic tool sets. In addition to specific content to be loaded into products, the knowledge exchange will provide access to related information including papers, posts, videos, and blogs on the same topic. In one embodiment a case study will contain a reference image set with associated contouring and segmentation of organs or structures of interest, treatment plan parameters, an achieved plan, follow-on care path for the patient represented in the case study, and what the long-term outcome for the case study patient was. In other words, the case study will have captured and presented the whole patient history. Further, each individual component of the case study (image set, contouring, segmentation, treatment plan parameters, etc.) has individual value and potential consumer clinicians may wish to borrow/purchase only individual pieces of the case study and apply it to their current patient, or borrow/purchase the entire case study and apply the entire case study to their patient as a complete methodology of treatment.

The tool sets are able to directly read the parametric information of these downloaded case studies. With the ability to transfer information that has clinical value, that's parametric to patients, and with the ability to socially network, putting that together around reference case studies and current medical cases in need of solutions, there is now a new way of communicating clinical best practices. The consumer clinician can download a case study, register a reference image set to a medical image set for the current patient and bring in parametric data from the downloaded case study into the treatment plan and make any necessary adjustments, as discussed below. The consumer clinician therefore has a valuable starting point. For example, the case study comprises the parameters used in the case study, descriptors describing the rationale behind the parameters, and a case description of the case study, thereby providing the consumer clinician with the full context of the case study (in other words, lecture, theory, practice, a full suite of parameters, and instructions to accomplish a complete radiotherapy treatment planning session).

Figure 1:
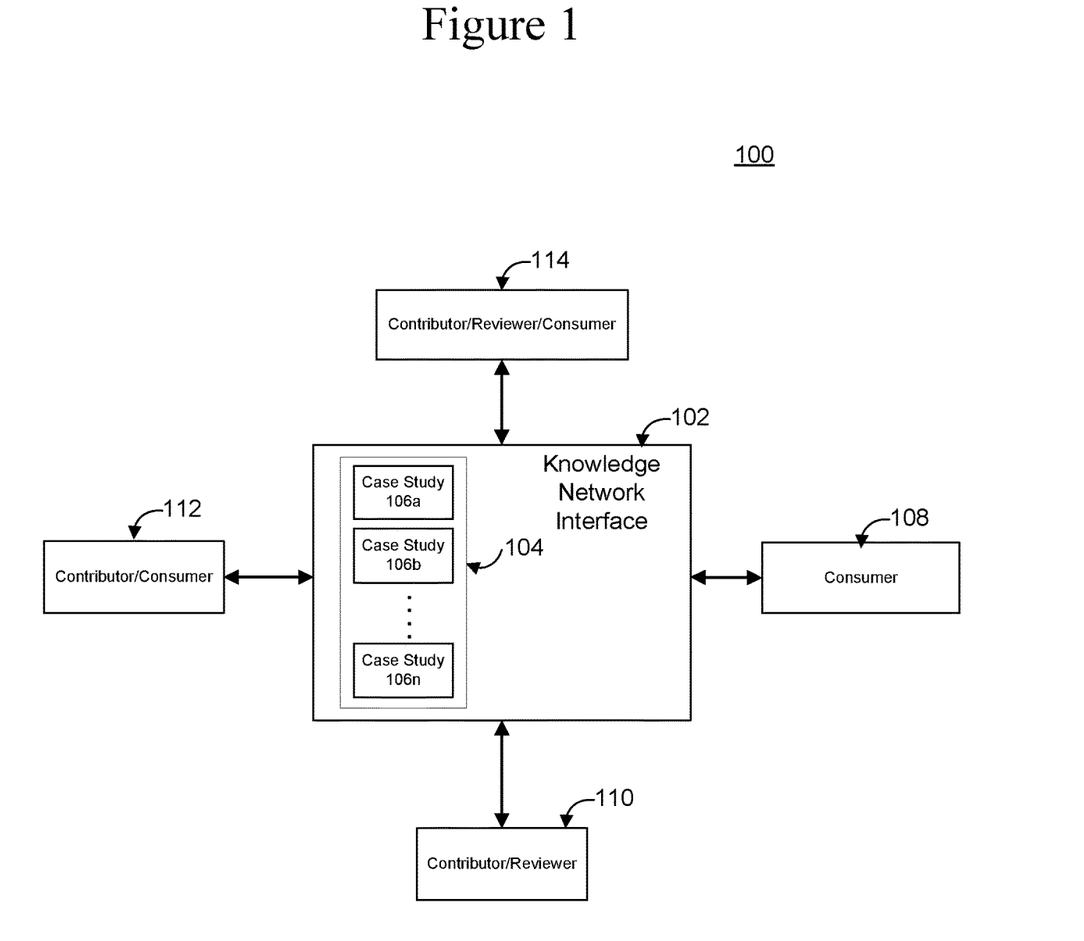
FIG. 1 is a simplified block diagram illustrating an embodiment of a knowledge-based radiation treatment exchange, in accordance with an embodiment of the present invention.

FIG. 1 illustrates an embodiment of a knowledge exchange 100. The knowledge exchange 100 in FIG. 1 comprises a knowledge exchange interface 102 that includes a database 104 comprising a plurality of individual case studies 106a-106n. FIG. 1 illustrates that various types of users will be connected to the knowledge exchange interface 102. These users include consumers 108, contributor/reviewers 110, contributor/consumers 112, and contributor/reviewer/consumers 114. A consumer 108 is defined as a clinician who wishes to download and use a case study as a reference and starting point for a specific case across the clinical process. A contributor/reviewer 110 is defined as a clinician who wishes to upload case studies for others to download and use or review, as well as one who wishes to download case studies to review them. Such reviewers 110 may be taking part in the peer review process for submitted case studies 106, as well as reviewing the results achieved when a consumer clinician 108 has downloaded and used one of the contributor/reviewer's 110 submitted case studies 106 and is now seeking feedback. In one embodiment it is anticipated that after a consumer downloads a selected case study from a particular contributor and applies the case study to their specific patient case, the contributor will be able to review the consumer's results and provide advice and feedback as to the achieved results. In another embodiment it is also anticipated that the consumer will be able to seek advice, review, and feedback from the contributor as well as other reviewers who may be interested in providing the desired review and feedback. A contributor/consumer 112 is defined as a clinician who wishes to upload case studies to the knowledge exchange for peer review and use by others, as well one who wishes to download and use a case study as a reference and starting point for a specific case across the clinical process. Finally, a contributor/reviewer/consumer 114 is defined as a clinician who wishes to contribute case studies to the knowledge exchange for peer review and use by others, to review case studies of others as part of the peer review process as well as reviewing the results of those who've downloaded their submitted case studies to use, and finally as one who also wishes to download and use a case study as a reference point starting point for a specific case across the clinic process. All knowledge exchange participants mentioned above download and/or upload content to or from the knowledge exchange, such that all reviewing, editing, and applying of case studies to specific patient cases takes place within tool sets off line.

Contributing to the Knowledge Exchange

In an exemplary embodiment, a clinician who plans to publish a paper on the use of a particular tool set for head-and-neck cases could log onto the knowledge exchange website and upload the clinical case study information, including contours, treatment plan, care plan, and prescription. The submitted clinical case study or studies would be the intellectual property of the clinician who posted the case study; therefore, the contributor dictates the IP status and price to download (if any). This posting can also include related papers, images, videos, and comments.

In one embodiment, when a contributing clinician posts a case study to the knowledge exchange, the contributing clinician may host a chat room to support questions and discussion around that particular case study. Further, clinicians who either review or download the case study (e.g., to use the case study) will be able to post in the chat room to discuss the reviewed or downloaded case study.

Rating and Quality Control

In one embodiment, users of the knowledge exchange will be able to rate the quality of submitted case studies using for example, a 5-star rating system. Further, these reviewers will also be able to write a review of the clinical content of the reviewed case study. The ratings associated with each clinical case study belonging to a contributor will also be aggregated to create an overall reputation rating for the contributing clinician. The scoring system can be used as incentive for individuals in the knowledge exchange community, and can be used by an embodiment of the system to recognize prolific and high-quality contributors.

Initially, an embodiment will establish a clinical advisory board to preview all case studies before allowing them to be published; however, once the knowledge exchange is fully established, it is expected that the community will be able to self-police effectively. In another embodiment, the clinical advisory board will be maintained to recognize and certify popular and highly rated contributions. In discussion forums, blogs, and case study reviews, positive and negative posts about the knowledge exchange and other user-interactive networks, will be permitted, although the Knowledge Exchange will be monitored and offensive or irrelevant items will be removed as needed. In cases of extreme abuse, blatant misrepresentation, or by request of credible members of the community, specific contributors may be banished from the community.

Such ratings for individual case studies as well as ratings for contributing clinicians with the addition of "expert" case studies and the recognition of particular contributing clinicians with expertise in particular areas will be immediately useful to potential consumer clinicians. For example, some contributing clinicians will be experts in treating a particular form of disease and their expertise will be highly valued and sought after by others. In other words, the rating system allows consumer clinicians to know who the expert contributing clinicians are as well as knowing what are considered by the knowledge exchange community (as well as by the clinical advisory board) to be expert case studies. This allows a consumer clinician to provide a treatment plan methodology of a distant team of experts for his own patient. As noted above, the treatment plan methodology may contain all or part of the electronic contents of the case study.

Each contributing clinician will have a rating and each contributed case study will have its own peer rating. Therefore, when a consumer clinician searches the database of case studies in the knowledge exchange they may request case studies submitted from clinicians with at least a minimum aggregate rating score (which may also be referred to as a reputation score, based upon an aggregate of the ratings of their submitted case studies) and case studies with a minimum peer review rating.

In one embodiment, to promote the contribution of case studies and the reviewing of submitted case studies (from contributing clinicians) and applied case studies (from consumer clinicians), contributing and reviewing clinicians may receive a kind of "currency" for each case study they submit or review. Such a currency may in embodiments of the knowledge exchange be spent, for example, by purchasing case studies to download and use at a discount.

A Consumer Wishing to Use the Knowledge Exchange

An exemplary consumer clinician interested in head-and-neck treatments would follow an exemplary process comprising the following steps:
1. Log onto the knowledge exchange website where they would enter the type of case, diagnosis and stage, and tool set treatment technique into the search engine. As discussed in detail below, there are other search criteria also available. If this was the first time they had logged onto the knowledge exchange, they would also need to setup a user name/password, as well as setup a new user account.
2. The search engine will return several cases posted by other contributing clinicians as well as related posts, videos, and blogs on the same topic.
3. The consumer clinician can browse the profiles of various contributors, read the reviews of various case studies, and chose one that best meets their needs.
4. The consumer clinician in one embodiment makes an electronic payment to the poster (the host providing the service will take a nominal commission) and downloads the case study. A fee (if any) for downloading the case study will be set by the contributing clinician.
5. The case study will be formatted for the particular clinical tool set the consumer clinician utilizes and automatically loaded into the target tool set.
6. Once downloaded, the consumer clinician is able to modify the case study for their clinic and apply it to an individual patient. The clinician can read any attached papers and watch any videos or other presentations. Additionally, they may post questions about the case for the clinical community to help answer. It is anticipated that as discussed above and below, one member of the clinical community that will be available to provide review and feedback will be the clinician who contributed the downloaded case study to the knowledge exchange.

The consumer clinician after downloading the desired case study will be able to load the case study into their own tool set and have an example to show them what the final result in the case study looked like, as well as how it looks in their own medical image set (deformable image registration used to deform the reference images to the medical image, as discussed in detail below). Therefore, the consumer clinician can compare their prepared treatment plan to the treatment plan in the downloaded case study. This allows the consumer clinician to look at the final result of the case study and compare it to their own results and then make any adjustments to their own treatment plan based upon the downloaded case study. In other words, the knowledge exchange allows the consumer clinician to compare their own results relative to some standard, which can be especially useful when it is a particular medical condition that the consumer clinician has limited experience with.

The Knowledge Exchange Interfacing with a Tool Set

Figure 2:
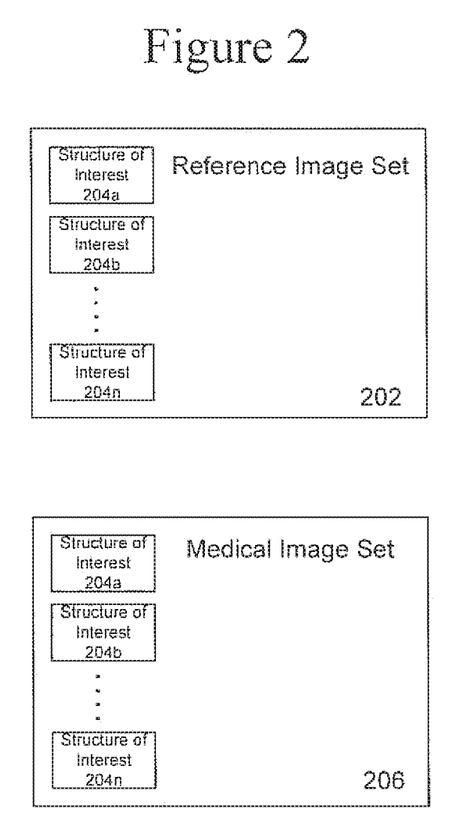
FIG. 2 is a simplified block diagram illustrating reference image sets and a medical image set, in accordance with an embodiment of the present invention.
Figure 3:
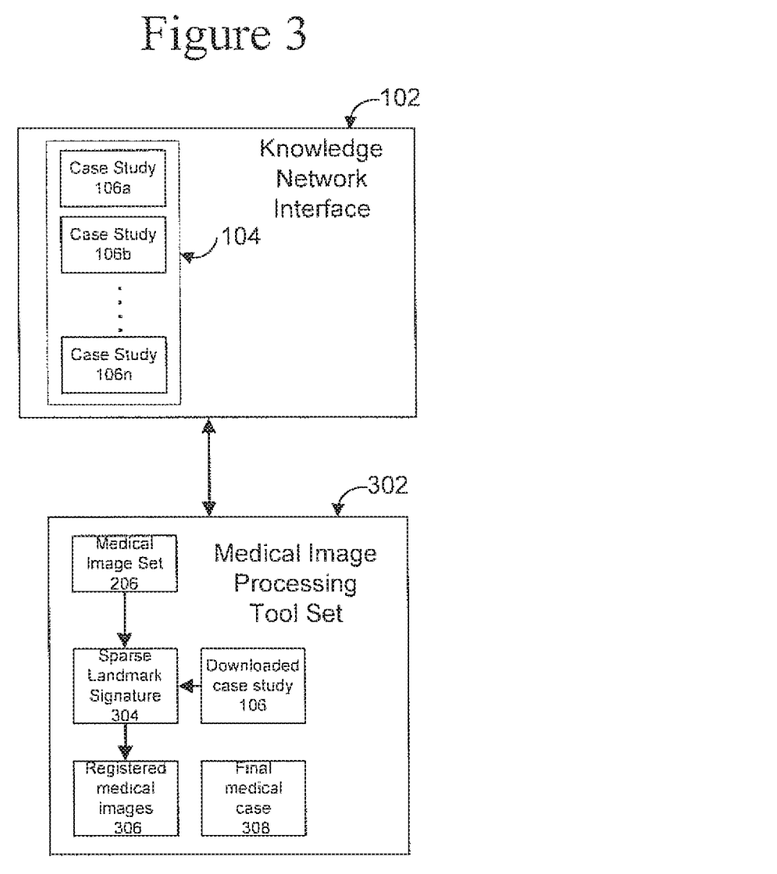
FIG. 3 is a simplified block diagram illustrating an embodiment of a knowledge-based radiation treatment exchange, in accordance with an embodiment of the present invention

FIGS. 2 and 3 illustrate an embodiment of the knowledge exchange interfacing with an exemplary tool set. The contents of an electronic case study, as discussed above, comprise a metadata file, pdfs, other text documents, audio/video files and an executable to run on the particular tool set. The tool sets are able to directly read the parametric information of these downloaded case studies. Such a tool set provides for example automatic contouring and automatic segmentation of each of the two-dimensional cross-sectional slices used in forming a three-dimensional image according to the rule set provided in the case study, such that the reference image set may be applied to the medical image set. Such an image set is discussed by Zankowski, in pending U.S. patent application Ser. No. 12/845,358, filed Jul. 28, 2010, entitled "Knowledge-Based Automatic Image Segmentation," which is incorporated herein by reference. As illustrated in FIG. 2 and discussed by Zankowski in the above patent application, each downloaded case study 106 comprises a reference image set 202 with a plurality of two-dimensional slices. A reference image set 202 also comprises meta-data, a sparse landmark signature corresponding to the reference image, and a plurality of segments and contours corresponding to structures of interest 204a-204n seen in each individual reference image slice. As further discussed by Zankowski, the particular patient case in the particular tool set includes a medical image set 206 with a plurality of two-dimensional slices. The medical image set 206 also includes a plurality of structures of interest 204a-204n seen in the individual two-dimensional slices of the medical image set 206, but without contouring and segmentation.

The tool set processes the medical image set 206 to reduce each slice of the medical image set 206 to a sparse landmark signature. In an embodiment of the present invention, and as discussed by Zankowski, the sparse landmark signature set made of all the sparse landmark signatures of the individual slices are also used in the selection process to find a suitable reference image set. Such use of the sparse landmark signature set may also be used to select a suitable case study. After a particular case study 106 has been selected and downloaded by the consumer clinician, the reference image set 202 of the selected case study 106 is deformed to the medical image set 206 in the tool set. In other words, the points in the sparse landmark signature of the reference image set 202 (one slice at a time) is deformed to the points in the sparse landmark signature set 304 of the medical image set 206.

In one exemplary embodiment, a deformable image registration algorithm will take the selected reference image set 202 and the medical image set 206, which has no segmentation or contouring and morph the reference image set 202, one slice at a time, to look like the medical image set 206. The registration algorithm will also transfer the contours from the reference image set 202 to the medical image set 206 as well. Therefore, each of the points from the reference image set 202 are deformed to the points of the medical image set 206. After the consumer clinician reviews and makes any manual adjustments to the results as seen in the now contoured and segmented medical image set 206, the consumer clinician is able to upload the results to the knowledge exchange to seek feedback on how well the contours and segmentations fit the organs or structures of interest 204a-204n in the medical image set 206.

FIG. 3 illustrates an embodiment of the knowledge exchange 100 interfaced with a particular tool set 302. In one embodiment, the tool set 302 is a medical image processing tool set described by Zankowski in the above referenced pending patent application. The medical image processing tool set 302 receives a downloaded case study 106 that comprises a reference image set 202. As illustrated in FIG. 3, after the medical image processing tool set processes the current medical image set 206 to produce the sparse landmark signature set 304, the reference image set 202 is registered to the medical image set 206 to create a registered medical image set 306. Such a registered medical image set 306 is therefore ready for consumer clinician review and editing as well as uploading back to the knowledge exchange 102 for further review and feedback from the clinical community as well as by the clinician who contributed the selected case study 106. After the uploaded registered medical image set 306 and other associated electronic contents (e.g., dose, radiotherapy treatment plan, etc.) making up the current medical case are downloaded and reviewed by the contributing clinician and any others selected by the consumer clinician, any provided feedback and editing of proposed contouring or treatment plans (for example) are reviewed by the consumer clinician, who after incorporating any desired changes creates a final medical case 308. The final medical case 308 comprises the final medical image set 306 as well as associated electronic contents mentioned above.

In addition to rule sets for applying the reference image set to the medical image set, as described above, a case study also includes a contoured and segmented reference image set as an example for comparison. This example contouring and segmenting provides a reference set to compare with what the consumer clinician has come up with.

When a consumer clinician has downloaded a case study and applied it to their patient, they have the ability to use the knowledge exchange to communicate directly with the contributing clinician, as well as anyone else they wish to communicate with. This will allow the consumer clinician to seek outside opinions, advice, and comment. The contributing clinician (and anyone else the consumer clinician has allowed) will be given access to the consumer clinician's applied treatment plan through the knowledge exchange, where they can download the applied case (deformed image set, contours, treatment plan, etc.) and view/edit it in their own tool set, including the ability to provide feedback comprising comments and suggestions as well as actual editing to the uploaded applied case, which will be sent back to the consumer clinician.

In an additional embodiment of the knowledge exchange, consumer clinicians, when they submit an applied case to the knowledge exchange for review by the associated contributing clinician, will also be able to request that other reviewing clinicians with acknowledged expertise in particular areas improve upon their applied case in those particular areas. Each reviewing clinician would review that portion of the applied case where they have expertise. The final result, with feedback, will provide what the peer acknowledged "experts" in each particular field can do in each area of the applied case, providing the best treatment plan for the consumer clinician's patient. Therefore, after this feedback into a derivative case, based upon an expert case study, the consumer clinician would be able to upload their own "expert case." It would provide an additional example of what might be a rare case.

In one embodiment, consumer clinicians will be able to upload their applied case to the knowledge exchange and place it into a public network that other members of the knowledge exchange community will be able to see and access. For instance, an expert in head cases could volunteer to review all submitted brain cases (improving the contouring of these brain cases that have been submitted for review and feedback). In other words, a reviewing clinician may set it up so that the knowledge exchange notifies them whenever a particular kind of case gets posted to a public network for review within the knowledge exchange. It is anticipated that when potential reviewers see that a consumer clinician has posted an applied case to a public network, they will be able to ask the consumer clinician if they would like them to review the case. Such communication may take place through email, instant message, blogs, or chat rooms, for example.

Such participation of clinician reviewers allows the knowledge exchange community to help further define what are best practices and to ensure that consumer clinicians who are downloading case studies and seeking review and feedback have access to what is considered the current best practice. Such community cooperation will also ensure that protocol development for current technology continues, allowing the review of the actual use of the technology (e.g., currently used tool set).

Figure 4:
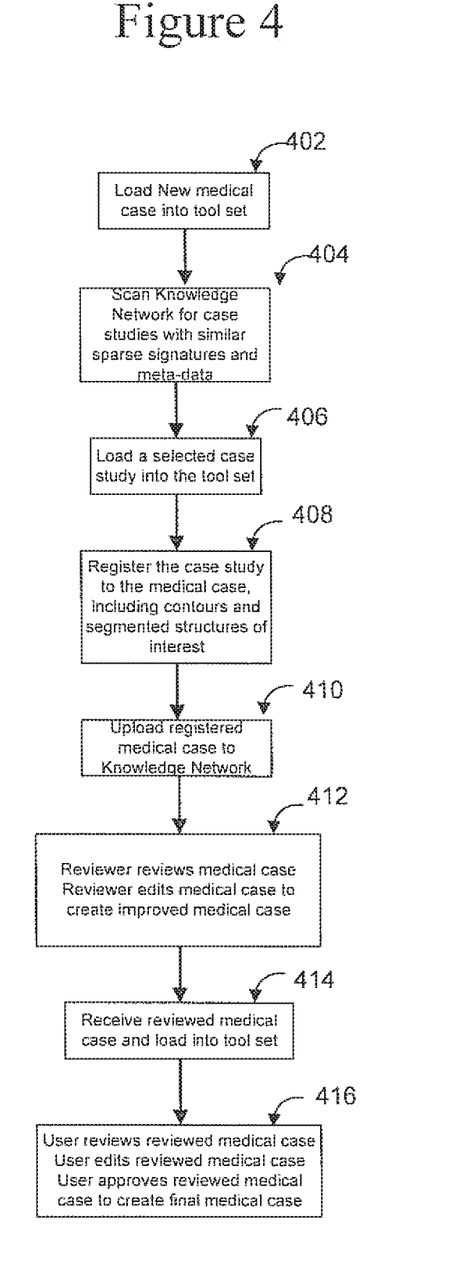
FIG. 4 illustrates steps of example processes for implementing a radiation therapy knowledge exchange, in accordance with an embodiment of the present invention.

FIG. 4 illustrates a flow diagram for a consumer using the knowledge exchange. In step 402 a medical case is loaded into a tool set 302. In one embodiment, after loading the medical case into the tool set 302, a medical image set 206 is reduced to a sparse landmark signature set 304. In step 404 the knowledge exchange is searched for case studies 106a-106n with similar sparse signatures and meta-data. In step 406, the selected case study 106 is downloaded and loaded into the tool set. In step 408, a reference image set 202 of the selected case study 106 is registered to the medical image set 206 of the medical case. In registering the reference image set 202 to the medical image set 206, the contours and segmented structures of interest of the reference image set are also registered to the medical image, such that the points of the sparse signature set of the reference image set 202 match the sparse signature set of the medical image set 206. In step 410, the registered medical case, which includes the registered medical image set 306, is uploaded to the knowledge exchange. In step 412, a selected reviewer downloads and reviews the registered medical case. In reviewing the registered medical case, the contours and segmentation for the medical image set are also reviewed, along with the proposed radiotherapy treatment plan and other associated treatment steps. The selected reviewer may be the contributor of the selected case study or another clinician who provides a review and feedback to the consumer clinician. In step 414, the reviewed medical case is returned to the consumer clinician (through the knowledge exchange) and loaded into the tool set 302 for review. In step 416, the downloaded reviewed medical case is reviewed by the consumer clinician and any necessary changes are made to create a final medical case. In one embodiment, the consumer reviews the reviewed medical case which contains an edited registered medical case, and after any other changes, saves the reviewed medical case as a final medical case. In another embodiment, the consumer reviews the reviewed medical case which contains an edited registered medical case and incorporates any desired changes from the reviewed medical case into the registered medical case to create a final medical case.

Figure 5A:
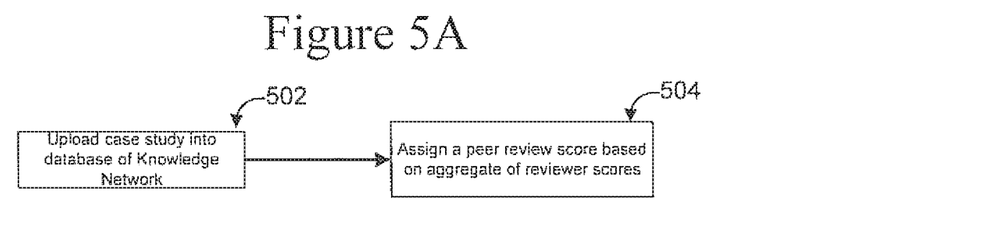
FIGS. 5A-5C illustrate steps of an example process for implementing a radiation therapy knowledge exchange, in accordance with an embodiment of the present invention.

FIG. 5A illustrates steps to a procedure for uploading and peer reviewing a case study submitted by a contributing clinician. In step 502, a contributing clinician uploads a case study into the database of the knowledge exchange. The uploaded case study will contain electronic records comprising: a reference image set, radiation therapy prescriptions, delineation of organs, tumors and regions within the reference image set for treatment planning (contours and segmentation of organs and/or structures of interest), radiation therapy treatment planning, and radiation therapy treatment protocols and process descriptions, etc. In step 504, the uploaded case study is downloaded and peer reviewed. In peer reviewing, each reviewer who downloaded the submitted case study assigns a rating (e.g., selecting a numerical rating of 1-5) and optionally drafts a written review of the submitted case study. In one embodiment, the submitted case study will also be reviewed by a clinical advisory board that previews all case studies before allowing them to be published. However, any member of the knowledge exchange community (consumers, providers, and other clinicians) will be able to download and review submitted case studies to help contribute to a peer rating for the submitted case study. In another embodiment, the clinical advisory board will be maintained to recognize and certify popular and highly rated contributions.

Figure 5B:
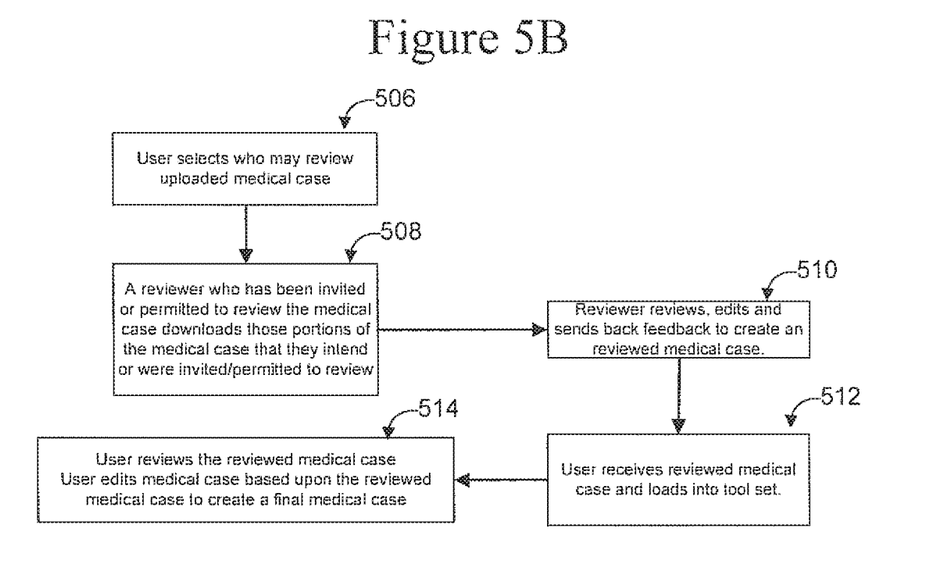

FIG. 5B illustrates steps to a procedure for receiving reviews and feedback after downloading and applying components of a case study to a current medical case. In step 506, the consumer clinician selects who they wish to review a registered medical case that is ready for review. In one embodiment, the consumer clinician selects a single reviewer, such as the contributing clinician who authored the selected case study. In another embodiment, the consumer clinician may select a different reviewer to review the registered medical case. In step 508 the selected reviewer downloads the registered medical case. In one embodiment, an individual reviewer may be able to download the entire medical case uploaded for review, or only a portion of it. In other words, there may be only portions of the medical case that have been submitted for review. In step 510, the selected or permitted reviewer reviews the downloaded medical case. In reviewing the submitted medical case, a reviewer may merely provide written feedback or in addition may edit the contents of the medical case submitted for review (e.g., adjusting the position of the contours in the medical image set and adjusting the radiation therapy prescription, etc.). After completing the review, the feedback is sent to the consumer clinician (through the knowledge exchange). Such feedback may be as simple as a text document or the submitted medical case with editing such that it is now considered a reviewed medical case. In step 512, the consumer clinician receives the feedback from a reviewer. When the feedback is in the form of a reviewed medical case, it is loaded into the tool set for further review by the consumer clinician. In step 514, the user reviews the downloaded feedback and/or reviewed medical case, edits the registered medical case based on the feedback and creates a final medical case that may be used to treat the patient.

Figure 5C:
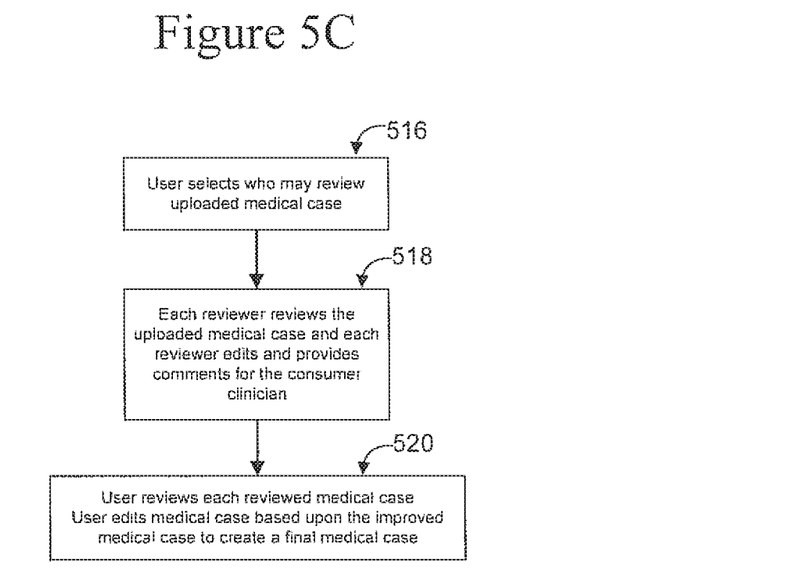

FIG. 5C illustrates steps for a further implementation of a method for enabling multiple reviewers to submit reviewed medical cases to the consumer clinician. In step 516, the consumer clinician selects which reviewers they desire to review the medical case. The medical case is also uploaded to the knowledge exchange. The submitted medical case comprises radiation therapy prescriptions, delineation of organs, tumors and regions within the medical image set for treatment planning (contours and segmentation of organs and/or structures of interest), radiation therapy treatment planning, and radiation therapy treatment protocols and process descriptions, for example that are based upon the downloaded case study that was applied to the medical case with the tool set. In step 518, each reviewer of a plurality of reviewers are downloading and reviewing the submitted medical case. When reviewing, each reviewer will separately review the submitted medical case and provide separate feedback to the consumer clinician (through the knowledge exchange). In reviewing the submitted medical case, a reviewer may merely provide written feedback or in addition may edit the contents of the medical case submitted for review (e.g., adjusting the position of the contours in the medical image set or adjusting the radiation therapy prescription, etc.). After completing the review, the feedback is sent to the consumer clinician (through the knowledge exchange). Such feedback may be as simple as a text document or the submitted medical case with editing such that it is now considered a reviewed medical case. In step 520, the consumer clinician receives feedback from the plurality of reviewers. The consumer clinician downloads and reviews the feedback provided and incorporates those portions of the feedback that they approve of into the medical case to create a final medical case. When a plurality of reviewers have provided feedback, each feedback will be reviewed separately and incorporated into the submitted medical case to create a final medical case. In other words, the consumer clinician may be required to consolidate feedback from multiple reviewers into a single suggested change for the submitted medical case or a plurality of changes. It may also be necessary for the consumer clinician to send out an updated medical case for further review by the same reviewers, a portion of the original reviewers, or selected different reviewers. This may especially be the case when several of the reviewers have suggested contradictory corrections to the medical case.

Capabilities of the Knowledge Exchange During Implementation

An implementation embodiment of the knowledge exchange comprises implementations involving web-enabled clinical collaboration, IP infrastructure, Tool Set modifications, and a phased implementation plan.

A web-based infrastructure will be created to support knowledge exchange capabilities to allow the implementation of an online collaborative community. Such an online collaborative community will facilitate the exchange of best practice discussions between clinicians. This communication between clinicians will not be altered. The web-based infrastructure in this embodiment does not include an exchange of third-party applications. Third party applications exchange would be added to the Knowledge Exchange at a later phase.

An embodiment of the knowledge exchange will include a tool set with the ability to create, edit and save case studies to the knowledge exchange; add clinical content for the case including recommended prescriptions, treatment plans, and care paths; the ability to export cases and post them on the knowledge exchange website; download cases from the knowledge exchange and import them into the tool set; and an additional search parameter that recognizes different clinical tool sets and process.

In an exemplary embodiment, the knowledge exchange will undergo a phased implementation plan. Phase 1 will comprise the establishment of a collaborative website. The website will be available for posting and discussion of radiotherapy clinic topics. In the initial release it will not include the electronic clinical content files. This website will be for clinicians to post cases and provide each other advice on the cases. All required web infrastructure will be in place.

Phase II will comprise a proof of concept on digital clinical content. In parallel with the establishment of the collaborative website, work will begin on a proof of concept for digital clinical content. Two or three clinical sites will be selected. The ability to extract and reload clinical content by disease site, stage, and technology base, will be proven.

Phase III will comprise a pilot of a digital clinical content exchange. Upon completion of the proof of concept a pilot program will be launched focused on a specific disease site and technology and a selected group of customers. The pilot will be used to further refine the collaborative website and exchange implementation framework. In an exemplary pilot program, 5-10 participants may be initially targeted as knowledge contributors and 25-50 sites will be identified as knowledge consumers.

Phase IV will comprise the launch of a digital clinic content exchange on the website. This will merge the collaborative website and the ability to upload and download electronic clinical content together. Future phases will include the ability to link data sets and outcomes analysis, and the ability to upload and download third party applications which run on the product platform (tool set). In additional embodiments, available tool sets provided by third party companies may be marketed and sold as entities separate from the fundamental knowledge exchange. In further embodiments, an online tool set may be provided which is accessible through a further embodiment of the knowledge exchange and can be purchased for use on an as needed basis.

As discussed above, as technology and available methods improve, the gap between actual and best practice continues to widen. A mix shift from developed to emerging markets exacerbates the problem as the rapid growth in emerging markets means a shortage of trained personnel and infrastructure to support advance technology. Therefore, the following embodiments of the knowledge exchange provide the following benefits.

An embodiment of the knowledge exchange implementing only the collaborative website will allow clinicians to give each other advice and discuss clinically relevant topics, and will contribute to the sharing of best practices thereby improving the use of tool sets associated with embodiments of the knowledge exchange.

A recommended embodiment of the knowledge exchange will implement the collaborative website, enable the importing and exporting of clinical content from associated tool sets at a given website, and enable clinical content sharing on the collaborative website. Such an implementation will allow clinicians to share actual electronic case studies to increase direct sharing of best practices for a given technology platform or tool set, providing a platform enabling communication of best practices, allowing knowledge creators/authors and consumers to extract the maximum value from their investment in the knowledge exchange, and provide improved clinical safety by providing more clinical support tools.

A best solution embodiment of the knowledge exchange implements: the collaborative website; enabling the importing and exporting of clinical content from associated tool sets at a given website; clinical content sharing on the collaborative website; automatic aggregation of clinical data into a data warehouse for outcomes analysis such that clinical content can be substantiated with outcomes data; and allowing the sharing of third party applications that connect through an implementation's API. Such an implementation will link clinical decisions and processes in radiation oncology and medical oncology to patient outcomes. It will increase the development of advanced technology by further engaging partners to develop solutions on platforms (tool sets) associated with the present invention. And takes the collaborative strategy to the next step by linking the process definitions to outcomes and establishing a developer community.

Beneficiaries of the Knowledge Exchange

Patient: patients have a higher likelihood of being treated with the most effective and safest treatment available to the clinic in which they are treated. Patients may (if outcomes are reached) be able to review prognosis with their oncologist, and help select their own treatment based on reliable statistics.

Physicist: Peer recognition and networking, ability to share new techniques with the community; opportunity to make money by posting useful applications; greater productivity; and access to best practice in quality assurance for specific techniques.

Dosimetrist: Access to benchmarks for what is achievable for a given type of case; greater productivity; and peer recognition and networking.

Physician: Opportunity to share and discuss challenging cases with peers; tools to capture own best practice internally for their own use in later cases; examples of best practices in the form of expert clinical cases from others; and improved productivity (contouring, dose prescriptions) derived from the use of clinical cases.

Hospital Administrators: Content for administrators may consist of improved reports, dashboards, and enhanced marketability based on proven best practice and/or clinician ratings from the Knowledge Exchange community.

Implementers: Opportunity to hear firsthand what customers are saying to other customers about their products and the competitors; ability to receive direct customer feedback about implemented products; access to third party applications for eventual incorporation into the core platform; ability to listen in on peer to peer discussions regarding implemented products and tool sets, the website will provide an ongoing opportunity to learn how the implemented products are used, where they are effective, where they are deficient, and to see examples of how to improve product relevance; and the opportunity to learn more about how implemented products are used by customers.

Benefits of the Knowledge Exchange

The Knowledge Exchange will create a new, collaborative environment for clinicians. This new venue will increase the ability of clinicians to share best practices with each other, thereby increasing the safe and effective use of technology in treating cancer. Significant opportunities are available in developing product platforms for collaboration and engagement of customers and partners. Bringing these proven tools into Oncology will give the implementer the most comprehensive solution incorporating both products and services, with collaboration on clinical best practices.

As available tools sets for cancer treatments are advanced, more technology means more clinical choices and complexity. The key question is who will make the clinical choices to apply this technology and provide the "push button" simplicity necessary for safe, widespread adoption. Rather than the implementer of the knowledge exchange making these choices and "baking" them into the product, the digital clinical content concept enables clinicians to make these choices and offer them to other clinicians. The role of the implementer of the knowledge exchange then becomes one of enabling and sharing the clinical choices made by clinical experts.

The knowledge exchange can also be used as a repository for clinical research studies. Clinical studies in the knowledge exchange can be made available to practitioners who wish to participate in the study. Such clinical studies can focus on a particular treatment protocol. A protocol can be as simple as text documents describing a proposed treatment plan with specific treatment limitations (e.g., a particular tumor to receive a specific dosage, with surrounding organs receiving no more than a further specified dose level); to a more detailed treatment plan that approaches the complexity of an expert case. In one embodiment, the protocol itself can be tied with a particular expert case to aid in repeatability, such that the treatment described in the protocol of the clinical study will be carried out in conjunction with the use of the expert case. In further embodiments, the knowledge exchange can also be a repository for results of particular clinical research studies.

In an exemplary embodiment, an institution, such as one that contributes case studies as described above, may conduct a clinical study by creating an expert case as a form of protocol and solicit participants for a research study of this protocol. A private online community may be created for this purpose utilizing the knowledge exchange. Participating clinicians in the clinical study will download and use the above protocol (e.g., expert case) in their respective tool sets and then post their feedback and outcome data back to this private online community for review. Such efforts may be used to create a clinical study paper. This clinical study paper could then be submitted to peer reviewed journals and "published" in both traditional peer reviewed journals and in the public domain of the knowledge exchange with both items cross-referencing each other. Or the paper could be only "published" online through the knowledge exchange. The contributing institute will benefit in having focused research participants providing outcomes data, and the knowledge consumer institutions will benefit in participating in the clinic study by accessing advanced techniques and feedback on their use. Finally, the results of the research study as embodied in an expert case can be used by consumer clinicians as a basis for applying a treatment or planning protocol to a patient, with the clinical consumer and patient benefiting from the results of the research study.

Further, as best practices improve, clinicians will be able to connect an outcome with a protocol. The desire is so be able to connect all outcomes that followed particular protocols to show the results when particular protocols were followed. Therefore, the knowledge exchange will aid in linking protocols to outcomes to enable further outcome analysis for particular types of cases. In further developments, progeny of source protocols will also be linked to allow further analysis of protocols as they relate to outcomes.

Further Uses of the Knowledge Exchange

The Knowledge Exchange provides tools for the private capturing, sharing and reuse of proprietary clinical knowledge within a clinical setting. Some clinical locations will wish to extend this expertise to others as part of a business plan and branding strategy. The Knowledge Exchange enhances this business strategy by offering a delivery means to help ensure quality and comprehensiveness.

The Knowledge Exchange provides a method to deploy nationwide standards of care. The standards of care together with equipment and software may be deployed as part of a nationwide cancer initiative. The Knowledge Exchange helps achieve these clinical standards across geographically dispersed primary and secondary cancer centers.

Smaller and more remote clinical locations can use the Knowledge Exchange to collaborate with other clinics on difficult cases, in clinical adoption of new technology, and to share outcomes and best practices.

In parallel with improved platform technologies, academic and innovative centers can introduce clinical use cases which leverage the new technology clinically. In a manner similar to publishing papers, the Knowledge Exchange offers these centers a tangible way to gain reputation and prestige as leaders in the field of Radiation Therapy.

SUMMARIZING THE KNOWLEDGE EXCHANGE

In summary, the knowledge exchange will provide an electronic file containing a complete clinical template for an expert case including contours, treatment plans, and treatment protocols. The knowledge exchange will combine the electronic files, discussion forums, and related clinical information into an internet site that is searchable by type of disease, stage and clinical tool set, as well as other parameters discussed above. The knowledge exchange will allow a user (e.g., a clinician) to create and save their own clinical case for reuse and sharing with others. In the knowledge exchange, the clinical case is the intellectual property (IP) of the clinician posting the case. The poster can set the IP status and whether or not there will be a charge to download the case when posting. Lastly, other participants using the knowledge exchange will be able to rate a particular case study for its usefulness and assigning it a rating that will be linked to the case and the poster. These ratings can then be used to determine whether or not a posted case study will be considered an "expert case."

Although certain preferred embodiments and methods have been disclosed herein, it will be apparent from the foregoing disclosure to those skilled in the art that variations and modifications of such embodiments and methods may be made without departing from the spirit and scope of the invention. It is intended that the invention shall be limited only to the extent required by the appended claims and the rules and principles of applicable law.

What is claimed is:

1. A method implemented on a web-based infrastructure, the method comprising:
    storing a database comprising a plurality of case studies in memory of a first computer system, wherein the case studies include contours and segmentation of structures of interest in reference images and treatment plans;
    downloading a current medical case to the first computer system over the web-based infrastructure from the first computer system, wherein the current medical case includes medical images;
    reducing, with the first computing system, the medical images of the current medical case to a sparse landmark signature set;
    selecting, with the first computer system, a case study from the database, wherein the case study is selected based upon at least one similarity including sparse landmark signatures between the selected case study and the current medical case, wherein the current medical case comprises a first treatment plan for a first patient and wherein the selected case study is for a second patient different from the first patient, wherein the selected case study comprises reference images and also comprises a second treatment plan, and wherein the selected case study further comprises first outcome information describing the outcome of treating the second patient according to the second treatment plan;
    registering, with the first computer system, the selected case study to the current medical case based on the sparse landmark signatures including deforming the reference images of the selected case study to the medical images of the medical images of the current medical case and transfer contours from the reference images of the case study to the medical images of the current medical case;
    inputting, over the web-based infrastructure to a second computer system, at least a portion of the selected case study from the database into a tool set implemented on the second computer system that also accesses the current medical case from the first computer system over the web-based infrastructure, wherein the portion comprises the reference images;
    with the first computer system, determining a final version of the first treatment plan by incorporating feedback received over the web-based infrastructure into the first treatment plan, and adding the final version of the first treatment plan to the database, wherein the final version of the first treatment plan is based on the current medical case;
    accessing, with the first computer system and from the database, second outcome information describing the outcome of treating the first patient according to the final version of the first treatment plan; and
    with the first computer system, combining the final version of the first treatment plan, the second treatment plan, and the respective outcomes of the second treatment plan and the final version of the first treatment plan and creating a statistical link between the second treatment plan and the final version of the first treatment plan and the respective outcomes of the second treatment plan and the final version of the first treatment plan.

2. The method of claim 1, further comprising uploading the statistical link to a knowledge exchange system comprising the database.

3. The method of claim 1, wherein the portion of the selected case study is selected from the group consisting of: meta data of the selected case study, an image set, a document-based file, an image-based file, an executable, a contour, and a treatment protocol.

4. The method of claim 1, wherein the selected case study is stored as an electronic file comprising metadata that is selected from the group consisting of:
    weight, height, sex, age, race, size of patient, diagnosis, treatment site, whether or not there is nodal involvement, any co-morbidities, side of the body, and approximate location of tumor, stage, and desired treatment techniques.

5. The method of claim 1, further comprising:
    uploading, over the web-based infrastructure, the current medical case including the registered medical image set and the first treatment plan to a knowledge exchange system comprising the database after application of the portion of the selected case study, wherein said uploading the current medical case notifies reviewers that the current medical case is available for review;
    receiving, at the first computer system and from other devices coupled to the first computer system via the web-based infrastructure, a plurality of feedbacks from the reviewers on the current medical case; and
    receiving, at the first computer system, a final medical case based on the current medical case and the feedbacks, the final medical case including the final version of the first treatment plan.

6. The method of claim 1, further comprising adding the final medical case to the database as a new case study, wherein the new case study is stored with the plurality of case studies.

7. The method of claim 1, wherein each case study of the plurality of case studies is associated with a respective peer review score, and wherein a clinician that contributes a case study is associated with a reputation score.

8. The method of claim 7, wherein selecting the case study further comprises searching the database by at least one of: a minimum case study peer review score, and a minimum reputation score.

9. The method of claim 1, wherein at least one case study of the plurality of case studies is part of a clinical study.

10. A non-transitory computer readable media of a first computer system coupled to a web-based infrastructure, the non-transitory computer readable media comprising computer-executable instructions stored therein, the computer-executable instructions comprising:

instructions to store a database comprising a plurality of case studies in memory of the first computer system, wherein the case studies include contours and segmentation of structures of interest in reference images and treatment plans;

instructions to download a current medical case to the first computer system over the web-based infrastructure from the first computer system, wherein the current medical case includes medical images;

reducing, with the first computing system, the medical images of the current medical case to a sparse landmark signature set;

instructions to select, with the first computer system, a case study from the database, wherein the case study is selected based upon at least one similarity including sparse landmark signatures between the selected case study and the current medical case, wherein the current medical case comprises a first treatment plan for a first patient and wherein the selected case study is for a second patient different from the first patient, wherein the selected case study comprises reference images and also comprises a second treatment plan, and wherein the selected case study further comprises first outcome information describing the outcome of treating the second patient according to the second treatment plan;

registering, with the first computer system, the selected case study to the current medical case based on the sparse landmark signatures including deforming the reference images of the selected case study to the medical images of the medical images of the current medical case and transfer contours from the reference images of the case study to the medical images of the current medical case;

instructions to input, over the web-based infrastructure to a second computer system, at least a portion of the selected case study into a tool set implemented on a second computer system that also accesses the current medical case from the first computer system over the web-based infrastructure, wherein the portion comprises the reference images;

instructions to determine, with the first computer system, a final version of the first treatment plan by incorporating feedback received over the web-based infrastructure into the first treatment plan;

instructions to add, by the first computer system, the final version of the first treatment plan to the database, wherein the final version of the first treatment plan is based on the current medical case;

instructions to access, with the first computer system and from the database, second outcome information describing the outcome of treating the first patient according to the final version of the first treatment plan; and instructions to combine, with the first computer system, the final version of the first treatment plan, the second treatment plan, and the respective outcomes of the second treatment plan and the final version of the first treatment plan, to create a statistical link between the second treatment plan and the final version of the first treatment plan and the respective outcomes of the second treatment plan and the final version of the first treatment plan.

11. The non-transitory computer readable media of claim 10, wherein the computer-executable instructions further comprise instructions to upload the statistical link to a knowledge exchange system comprising the database.

12. The non-transitory computer readable media of claim 10, wherein the portion of the selected case study is selected from the group consisting of: meta data of the selected case study, an image set, a document-based file, an image-based file, an executable, a contour, and a treatment protocol.

13. The non-transitory computer readable media of claim 10, wherein the selected case study is stored as an electronic file comprising metadata that is selected from the group consisting of: weight, height, sex, age, race, size of patient, diagnosis, treatment site, whether or not there is nodal involvement, any co-morbidities, side of the body, and approximate location of tumor, stage, and desired treatment techniques.

14. The non-transitory computer readable media of claim 10, wherein the computer-executable instructions further comprise:
instructions to upload, over the web-based infrastructure, the current medical case including the registered medical image set and the first treatment plan to a knowledge exchange system comprising the database after application of the portion of the selected case study;
instructions to notify, over the web-based infrastructure, reviewers that the current medical case is available for review;
instructions to receive, at the first computer system and from other devices coupled to the first computer system via the web-based infrastructure, a plurality of feedbacks from the reviewers on the current medical case; and
instructions to receive, at the first computer system, a final medical case based on the current medical case and the feedbacks, the final medical case including the final version of the first treatment plan.

15. The non-transitory computer readable media of claim 10, wherein the computer-executable instructions further comprise instructions to add the final medical case to the database as a new case study, wherein the new case study is stored with the plurality of case studies.

16. The non-transitory computer readable media of claim 10, wherein each case study of the plurality of case studies is associated with a respective peer review score, wherein a clinician that contributes a case study is associated with a reputation score, and wherein the computer-executable instructions further comprise instructions to search the database for at least one of: a minimum case study peer review score, and a minimum reputation score.

17. The non-transitory computer readable media of claim 10, wherein the tool set imports and exports electronic content of case studies from and to another, different tool set using an application programming interface (API) that enables importing and exporting of the electronic content from and to the different tool set.

18. The method of claim 1, wherein the tool set imports and exports electronic content of case studies from and to another, different tool set using an application programming interface (API) that enables importing and exporting of the electronic content from and to the different tool set.

* * * * *